United States Patent [19]

Knothe et al.

[11] Patent Number: 4,798,252
[45] Date of Patent: Jan. 17, 1989

[54] DRYING BALANCE WITH TEMPERATURE CONTROL

[75] Inventors: Erich Knothe, Eddigehausen; Günther Maaz, Uslar; Volker Handwerk, Bovenden, all of Fed. Rep. of Germany

[73] Assignee: Sartorius GmbH, Fed. Rep. of Germany

[21] Appl. No.: 155,600

[22] Filed: Feb. 12, 1988

[30] Foreign Application Priority Data

Feb. 28, 1987 [DE] Fed. Rep. of Germany ....... 3706609

[51] Int. Cl.⁴ .................... G01G 19/00; G01G 21/28; G01N 25/56
[52] U.S. Cl. ................................. 177/245; 177/180; 73/76; 374/14
[58] Field of Search ...................... 177/180, 245, 200; 73/76; 374/14

[56] References Cited

U.S. PATENT DOCUMENTS 4,165,633  8/1979  Raisanen ..................... 177/245 X
4,291,775  9/1981  Collins ........................ 177/245 X
4,666,007  5/1987  Knothe et al. .................... 177/245

Primary Examiner—George H. Miller, Jr.
Attorney, Agent, or Firm—Eric P. Schellin

[57] ABSTRACT

A drying balance with a radiation source (11) for heating and drying a substance distributed on a balance scale (5), with a temperature sensor (8) for monitoring and controlling the output of the radiation source (11) and with electronic evaluating circuitry (33) for evaluating the measured values of the balance and for controlling the drying balance that a temperature gauging disk (14) with another temperature sensor built in be used in order to determine in a temperature gauging cycle the deviation of the output signal of the temperature sensor (8) from the output signal of the other temperature sensor built into the temperature gauging disk (14) and to calculate a correction factor from them and to store this correction factor. Then, the output signal of the temperature sensor (8) is multiplied by this correction factor during dryings in order to obtain the true temperature of the substance. Different coefficients of absorption of different substances can be mimiced by surfaces on the temperature gauging disk which exhibit different sizes and a high absorption capacity or a low absorption capacity.

8 Claims, 3 Drawing Sheets

DRYING BALANCE WITH TEMPERATURE CONTROL

BACKGROUND OF THE INVENTION

The invention relates to a drying balance with a radiation source for heating and drying a substance distributed on a balance scale, with a temperature sensor for monitoring and controlling the output of the radiation source and with electronic evaluating circuitry for evaluating the measured results of the balance and for controlling the drying balance.

Drying balances of this type are generally known, e.g. from the generic patent DE-GM No. 86 06 298. The geometric design of such a drying balance is shown e.g. in DE-OS No. 36 15 660.

However, the known drying balances have the disadvantage that the temperature sensor does not directly measure the temperature of the substance to be dried but rather is located only in the vicinity of the substance to be dried. A different radiation density at the location of the substance to be dried and at the location of the temperature sensor as well as, in particular, different coefficients of absorption for the radiation result in a temperature difference between the temperature sensor and the substance to be dried which varies in magnitude as a characteristic of the substance.

The invention therefore provides the solution of creating the means of measuring this temperature difference and of taking it into consideration when controlling the output of the radiation source.

SUMMARY OF THE INVENTION

The invention solves this problem as follows: A temperature gauging disk with a built-in additional temperature sensor is connected to the drying balance.

If the temperature gauging disk is positioned at the location of the balance scale and if it exhibits the same absorption properties as the substance to be dried, then it will also assume the precise temperature which the substance to be dried will assume. The adaptation of the absorption properties of the temperature gauging disk is performed in a first embodiment by covering it with a layer of the substance. To this end, the temperature gauging disk comprises a raised edge in an advantageous manner so that substance can be distributed on it like on a balance scale. In a second advantageous embodiment, the absorption property of the substance to be dried is imitated in that the surface of the temperature gauging disk is designed partially of graphite (high coefficient of absorption) and partially of aluminium (low coefficient of absorption). The real ratio is then selected in accordance with the absorption properties of the particular substance. This makes available an easy-to-handle secondary standard and the user of the drying balance need merely use such a secondary standard for each substance which may occur.

The temperature gauging of the drying balance is then performed with advantage in a gauging cycle in which the temperature gauging disk is inserted into the drying balance instead of the balance scale or on the balance scale and whereby the electronic evaluating circuitry sets a given temperature, compares the signals of the temperature sensor and of the additional temperature sensor in the temperature gauging disk with one another at this temperature and calculates a correction factor for the temperature sensor from the quotient. In the case of higher requirements made on the precision of the temperature control, two or more different temperatures are set in a corresponding manner and a gauging curve for the temperature sensor is calculated from them. This makes possible in the subsequent measuring cycles a correction of the signal of the temperature sensor to the true temperature of the substance to be dried.

The drying balance for carrying out this temperature gauging method therefore comprises, with advantage, memory and calculating means in the electronic evaluating circuitry which store a correction factor in the simple design and can change the signal of the temperature sensor by this correction factor, or which store the parameters of a gauging curve in the more precisional design and can convert the signal of the temperature sensor according to this gauging curve to the true temperature at the location of the substance to be dried. Thus, the results of the gauging curve are stored in the electronic circuitry of the balance and can be used for an automatic temperature correction without further input by the operator. In an especially advantageous embodiment the memory means are dimensioned in such a manner that correction factors or gauging curves for several substances can be stored and called by the operator.

BRIEF DESCRIPTION OF THE DRAWINGS

The invention is discussed below with reference made to the schematic drawings.

DETAILED DESCRIPTION OF THE INVENTION

Figure 1:
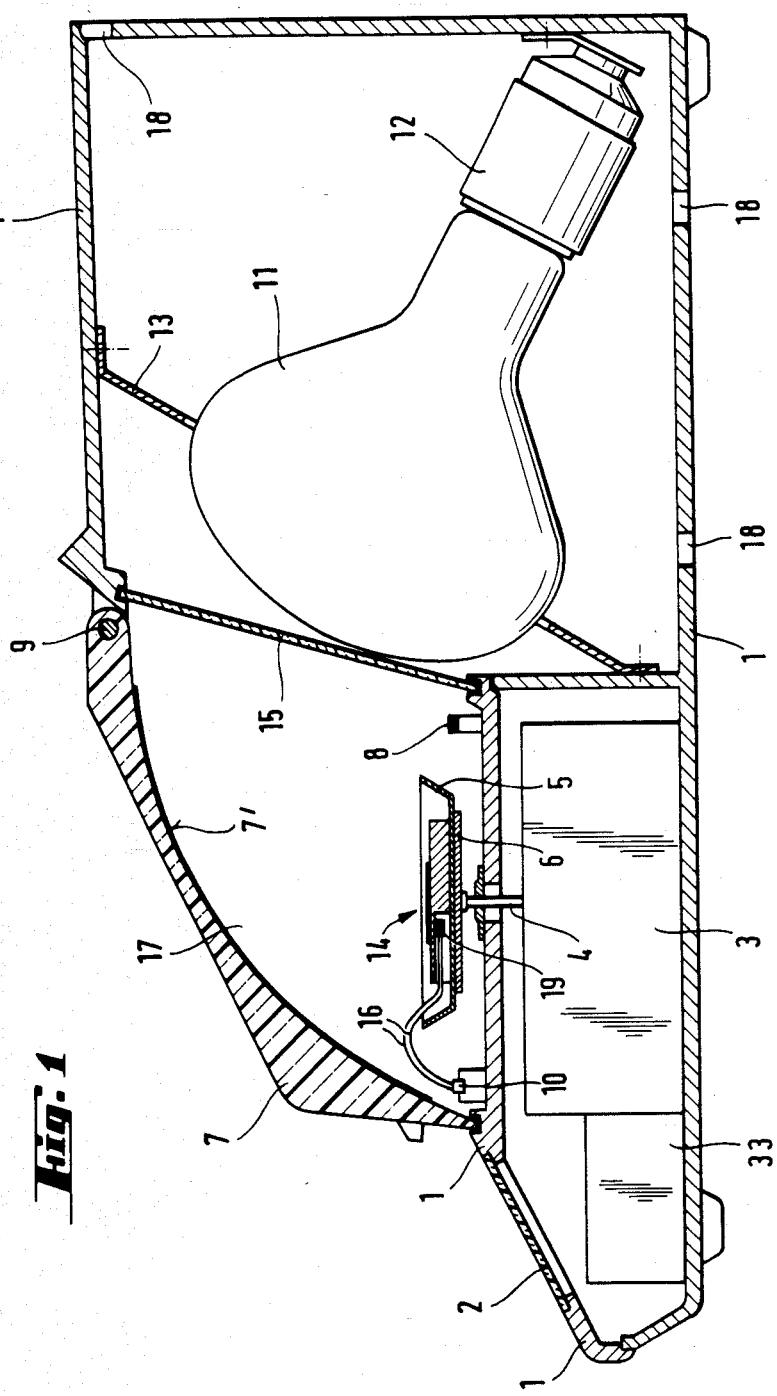
FIG. 1 shows the drying balance in section.

The drying balance in FIG. 1 consists of a multipartite housing 1 in which a weighing system 3 is housed. The type of this weighing system is immaterial for the invention; it can be, for example, a system based on the principle of the electromagnetic compensation of force. Scale support 6 is connected to weighing system 3 via component 4 for the introduction of force. Balance scale 5 with the substance to be dried and weighed rests in a removable fashion on scale support 6. Furthermore, observation window 2 is integrated into housing 1 which window permits the electronic display to be read. Radiation source 11, shown here as an infrared light, is located behind scale 5 and weighing system 3. Radiation source 11 is fixed to housing 1 by socket 12 and collar 13. The area of the radiation source is sealed off as regards air flow from weighing area 17 by means of wall 15, which can be permeated by the heat radiation. Ventilating and cooling of radiation source 11 is assured by perforations 18 in the bottom and the back side of housing 1. The drying balance also comprises a cover 7 which can be manufactured e.g. from plastic and comprises a reflecting coating on its inner side 7. This reflecting coating acts as a deflector for radiation and reflects the heat radiation form radiation source 11 onto the substance to be dried on scale 5. Cover 7 comprises rotatable bearing 9 on its back end so that it can be opened for loading the drying balance. Temperature sensor 8 for monitoring and controlling the output of radiation source 11 is fixed adjacent to scale 5 at a position at which the radiation density from radiation source 11 is, to the extent possible, just as great as the radiation density in the area of scale 5.

FIG. 1 also shows temperature gauging disk 14 with its connections 16, which rests in scale 5 and has approximately the same size as the latter. The temperature gauging disk comprises temperature sensor 19 (not shown in FIG. 1), e.g. a thermoelement or a temperature-dependent resistor or a temperature-dependent semiconductor. This temperature sensor 19 is connected via connections 16 and plug device 10 on housing 1 of the drying balance to electronic circuitry 33 of the balance.

Figure 2:
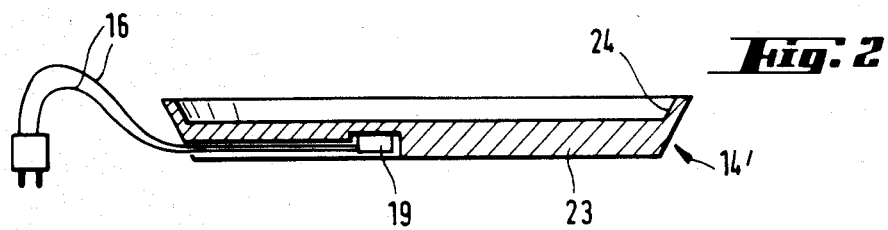
FIG. 2 shows a temperature gauging disk in a first embodiment in section.
Figure 3:
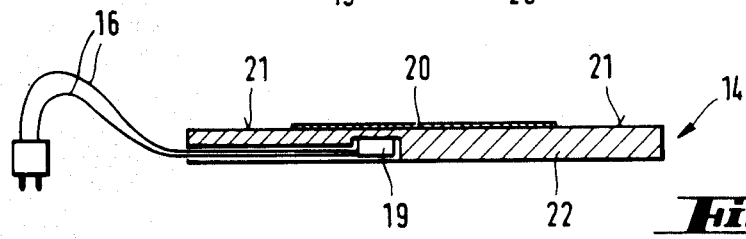
FIG. 3 shows a temperature gauging disk in a second embodiment in section.

The temperature gauging disk is shown in two embodiments in FIGS. 2 and 3 in section. Temperature gauging disk 14' in FIG. 2 consists of a sheet 23 with good heat conductivity with peripheral edge 24. Sheet 23 has a milled recess on the bottom into which temperature sensor 19 is inserted with its connections 16, which are only indicated. The substance to be dried can be distributed in a thin layer on sheet 23. Temperature gauging disk 14' is placed instead of scale 5 or together with scale 5 on scale support 6 of the drying balance, thus permitting the temperature to be measured directly on the substance and permitting a comparison with the temperature measured by temperature sensor 8. The weight value of the substance is distorted by leads 16 and temperature gauging disk 14' is therefore only used for one gauging cycle, as will be described further below.

Temperature gauging disk 14 shown in FIG. 3 contains no substance to be dried but rather the absorption behavior of the substance is imitated by the surface type of thick sheet 22. One part 21 of the surface consists of the smooth surface of aluminum sheet 22; another part 20 of the surface is covered with graphite. By suitably selecting the areal ratio of the two surface types, any coefficient of absorption between the low coefficient of absorption of the smooth aluminum and the high coefficient of absorption of the graphite can be mimicked. The determination of the areal ratio is made in practice by means of temperature gauging disk with substance according to FIG. 2 as primary standard. Then, the temperature gauging disk according to FIG. 3, which is much simpler to manage, can be used as secondary standard for the regaugings of the output control system for the radiation source, which are to be performed at certain intervals.

Figure 4:
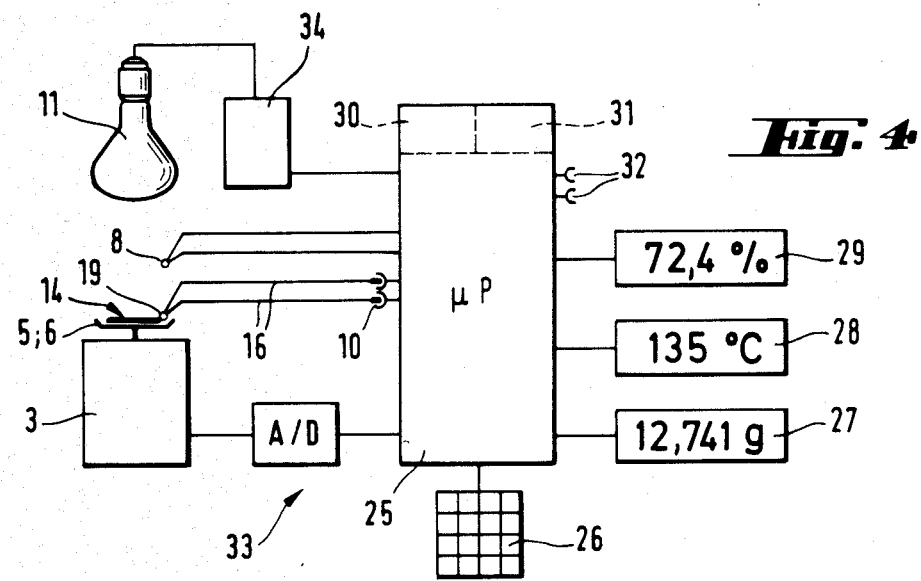
FIG. 4 shows a block diagram of the electronic circuitry of the drying balance.

Electronic circuitry 33 of the drying balance is shown in FIG. 4 in the form of a block diagram. Weighing system 3 carries scale support/scale 5/6 with temperature gauging disk 14. Radiation source 11 heats temperature gauging disk 14 as well as permanently built-in temperature sensor 8 during the gauging cycle. The output signals of the two temperature sensor 8, 19 are supplied to central electronic circuitry 25 and compared there. A correction factor is calculated from the two values and stored in memory area 30. Then, the output signal of temperature sensor 8 is multiplied by this correction factor during the measuring cycle (that is, without temperature gauging disk 14) before it is taken as true value for the output control of radiation source 11. The calculating means for multiplying by the correction factor are schematically indicated in FIG. 4 by 31. Central electronic circuitry 25 can be formed e.g. by a microprocessor in which these storage and calculating means 30, 31 are customarily present and can be appropriately programmed by any electronics expert without this having to be explained in detail here. FIG. 4 also shows readout unit 27 for the weight value, readout unit 28 for the true temperature, readout unit 29 for the amount of dry substance and recorder output 32 by way of example as well as keyboard 26 for operating the drying balance and for inputting numerical values.

Figure 5:
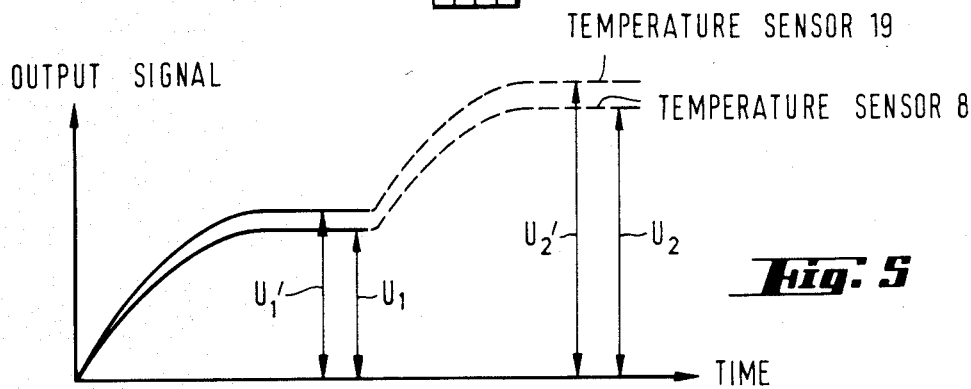
FIG. 5 shows the temperature course during a gauging cycle.
Figure 6:
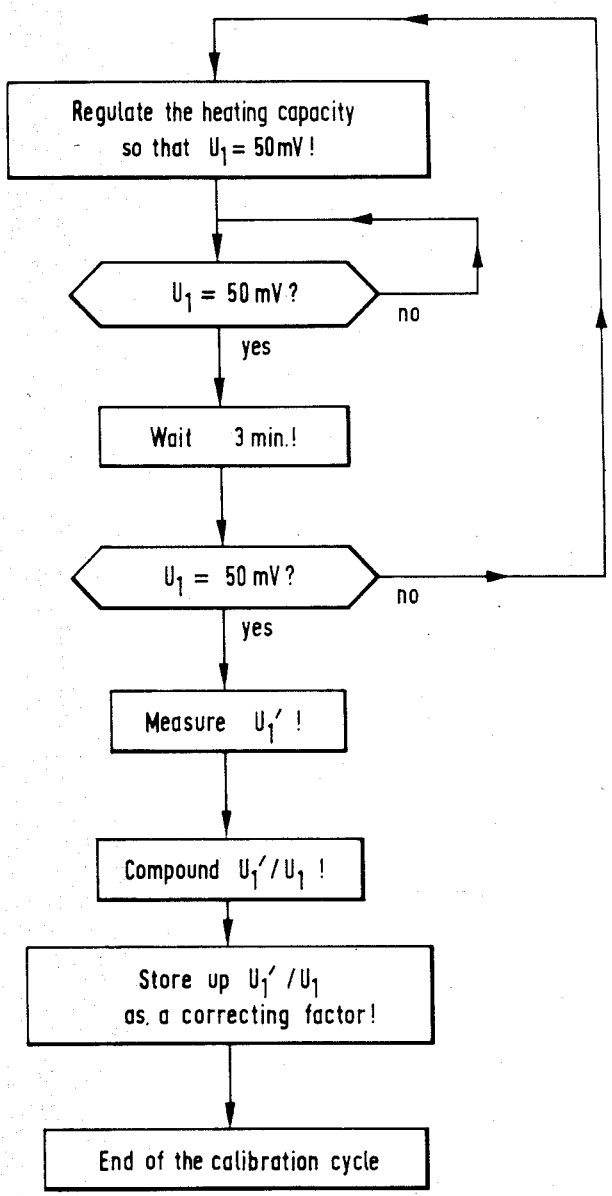
FIG. 6 shows a flow chart of the gauging cycle.

The operating sequence of a gauging cycle will now be explained with reference made to FIG. 5, 6. FIG. 5 shows the course of the output signals of the two temperature sensors 8, 19 as a function of the time; FIG. 6 shows a flow chart. At the start of the gauging cycle, the central electronic circuitry issues the order to adjust the heat output in such a manner that a constant temperature is begun. This temperature is given in the example by output signal $U_1$ of temperature sensor 8 of 50 mV. As soon as these 50 mV have been achieved at temperature sensor 8, a wait loop of e.g. 3 minutes duration begins in order to wait for a stable state. The maintenance of the constant temperature is then rechecked and then output signal $U_1$ of temperature sensor 19 in temperature gauging disk 14, 14' is measured. In the example, as is shown in FIG. 5, $U_1'$ is somewhat larger than $U_1$; thus, temperature gauging disk 14/14' is somewhat warmer than temperature sensor 8. The quotient $U_1'/U_1$ is calculated and stored as a correction factor. This ends the gauging cycle and temperature gauging disk 14/14' can be removed from the drying balance and measurements with substance to be dried can then be performed. In these measurements, the output signal of temperature sensor 8 is always multiplied by the stored correction factor and this calculated result is used as true value for the temperature control. In this manner, the temperature difference between the specimen and temperature sensor 8 determined in the gauging cycle is automatically corrected.

FIG. 5 also shows in dotted lines that in a more exacting embodiment of central electronic circuitry 25, not only one temperature (with output signals $U_1$ and $U_1'$) is started but that a second temperature is subsequently started. In the case of this temperature, the output signals $U_2$ and $U_2'$ of the two temperature sensor 8, 19 are compared in the same manner. For example, the quotient $U_2'/U_2$ can be formed again so that two correction factors for two different temperatures are calculated and stored. Then, the appropriate correction factor for any desired temperature is determined by linear interpolation.

In the case of one gauging point, only one correction factor can be calculated for all temperatures, in the case of two gauging points, it is possible to calculate a straight correction line and in the case of three gauging points, a correction curve can also be calculated. One of these possibilities is to be selected, depending on the requirement placed on the precision of adjustment of the drying temperature. In the case of one gauging point, it is placed with advantage in the vicinity of the most frequently used temperature; in the case of two gauging points, one is placed closer to the lower temperature limit and the other closer to the upper temperature limit; in the case of still more gauging points, they are distributed approximately equidistantly over the temperature range.

It is of course possible to store even more correction factors straight correction lines and correction curves for various substances by enlarging memory area 30. The appropriate correction values are then selected by inputting the substance number via keyboard 26.

What is claimed is:

1. Drying balance scale with a radiation source for heating and drying a substance distributed on a balance scale, with a temperature sensor for monitoring and controlling the output of the radiation source and with electronic evaluating circuitry for evaluating the measured sensed temperature values of the balance scale and for controlling the radiation source, characterized in that a temperature gauging disk with another temperature sensor built in is connected to the drying balance scale.

2. Drying balance according to claim 1, wherein the temperature gauging disk includes a raised edge so that a substance can be distributed on the temperature gauging disk.

3. Drying balance according to claim 1, wherein the temperature gauging disk includes a partial aluminum surface (21) and a partial graphite surface (20).

4. Method for the temperature gauging of a drying balance according to claim 1 wherein in a gauging cycle the temperature gauging disk is inserted into the drying balance instead of the balance scale or on the balance scale and is connected there and that the electronic evaluating circuitry sets a given temperature, compares the signals of the temperature sensor and of the other temperature sensor in the temperature gauging disk at this temperature and calculates a correction factor from the quotient for the temperature sensor.

5. Method for the temperature gauging of a drying balance according to claim 1 wherein in a gauging cycle the temperature gauging disk is inserted into the drying balance instead of the balance scale or on the balance scale and is connected there and that the electronic evaluating circuitry sets at least a low temperature and a high temperature, compares the signals of the temperature sensor and of the other temperature sensor in the temperature gauging disk with one another at these temperatures and calculates a gauging curve for the temperature sensor from them.

6. Drying balance for carrying out the method of claim 4, wherein a storage and calculating means are present in the electronic evaluating circuitry which store a correction factor and which can change the signal of the temperature sensor by this correction factor.

7. Drying balance for carrying out the method of claim 5 wherein a storage and calculating means are present in the electronic evaluating circuitry which store the parameters of a gauging curve and which can convert the signal of the temperature sensor in accordance with this gauging curve to the true temperature at the location of the substance to be dried.

8. Drying balance according to claim 7, wherein the storage means are designed in such a manner that correction factors or gauging curves can be stored for several substances.

* * * * *